(12) United States Patent
Simon et al.

(10) Patent No.: US 10,718,004 B2
(45) Date of Patent: Jul. 21, 2020

(54) DROPLET ARRAY FOR SINGLE-CELL ANALYSIS

(71) Applicant: Lawrence Livermore National Security, LLC, Livermore, CA (US)

(72) Inventors: Melinda Simon, Fremont, CA (US); N. Reginald Beer, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 875 days.

(21) Appl. No.: 15/385,799

(22) Filed: Dec. 20, 2016

(65) Prior Publication Data

US 2018/0171377 A1 Jun. 21, 2018

(51) Int. Cl.
*B01L 3/00* (2006.01)
*C12Q 1/24* (2006.01)

(52) U.S. Cl.
CPC .......... *C12Q 1/24* (2013.01); *B01L 3/502761* (2013.01); *B01L 3/502784* (2013.01); *B01L 2200/0652* (2013.01); *B01L 2200/0668* (2013.01); *B01L 2300/0816* (2013.01); *B01L 2300/0851* (2013.01); *B01L 2400/086* (2013.01)

(58) Field of Classification Search
CPC ..... B01L 2200/0652; B01L 2200/0668; B01L 2300/0816; B01L 2300/0851; B01L 2400/086; B01L 3/502761; B01L 3/502784; C12Q 1/24
See application file for complete search history.

(56) References Cited

U.S. PATENT DOCUMENTS

| 9,176,504 | B2 | 11/2015 | Chiou et al. | |
|---|---|---|---|---|
| 2010/0003666 | A1* | 1/2010 | Lee | B01L 3/502761 435/5 |
| 2011/0030808 | A1* | 2/2011 | Chiou | B01L 3/502738 137/13 |
| 2012/0122084 | A1* | 5/2012 | Wagner | G01N 15/1434 435/6.1 |
| 2013/0337500 | A1* | 12/2013 | Tan | G01N 33/5005 435/39 |

(Continued)

FOREIGN PATENT DOCUMENTS

| WO | 2006040551 A3 | 6/2006 |
|---|---|---|
| WO | 2007081385 A2 | 7/2007 |

OTHER PUBLICATIONS

Baret, J., et al., "Fluorescence-activated droplet sorting (FADS): efficient microfluidic cell sorting based on enzymatic activity," Lab Chip. Jul. 7, 2009;9(13):1850-8.

(Continued)

*Primary Examiner* — Jennifer Wecker
(74) *Attorney, Agent, or Firm* — Perkins Coie LLP

(57) ABSTRACT

Techniques, systems, and devices are described for implementing a droplet array for single-cell analysis. A method of conducting single-cell analysis comprises generating a plurality of droplets, wherein each of the plurality of droplets contains a core material surrounded by a protective shell; loading the plurality of droplets, via a carrying fluid, onto an array including a plurality of trap structures, wherein the plurality of droplets are held by the plurality of trap structures; selecting a target droplet, held by a trap structure, from the plurality of droplets; and releasing the target droplet from the trap structure.

28 Claims, 10 Drawing Sheets

(56) References Cited

U.S. PATENT DOCUMENTS

2014/0262787 A1* 9/2014 Molho ............. G01N 27/44756
    204/547
2017/0199173 A1* 7/2017 Konry ............... B01L 3/502784

OTHER PUBLICATIONS

Brouzes, E., et al., "Droplet microfluidic technology for single-cell high-throughput screening," www.pnas.org/cgi/doi/10.1073/pnas.0903542106; 6 pages.

Huebner, A., et al., "Static microdroplet arrays: a microfluidic device for droplet trapping, incubation and release for enzymatic and cell-based assays," Lab Chip. Mar. 7, 2009;9(5):692-8.

Ishii, S., et al., "Microbial metabolic networks in a complex electrogenic biofilm recovered from a stimulus-induced metatranscriptomics approach," Scientific Reports, 5, 14840, 2015.

* cited by examiner

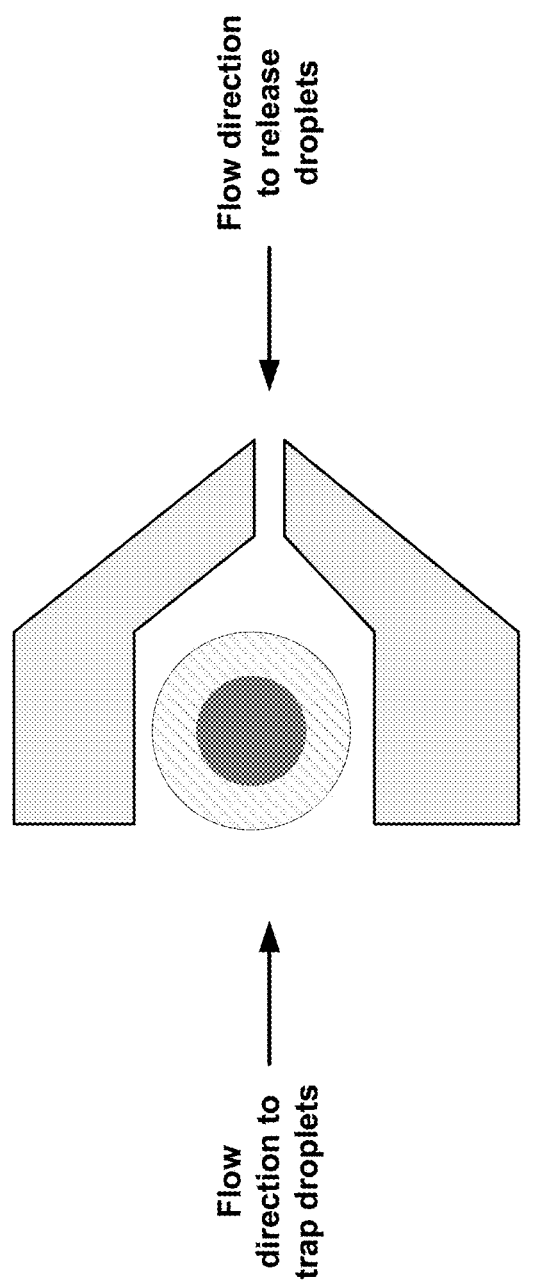

DROPLET ARRAY FOR SINGLE-CELL ANALYSIS

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

TECHNICAL FIELD

This patent document relates to systems, devices, and processes that use a droplet array to conduct single-cell analysis.

BACKGROUND

Enabling manipulation and observation of cells on a single cell level has been a major focus of microfluidics research for the past two decades. Such technologies would allow quantification of the degree of heterogeneity within a population of cells, which would otherwise be characterized by an averaged result obtained from analyzing the lysate of many cells. This is useful in screening populations of cells for a rare mutation, useful for diagnosis and genotyping of human disease and in commercial applications where mutations are induced to improve a product, such as in the agricultural industry.

Microfluidic droplets are useful to contain single cells in order to isolate the assays and characterization done on each cell. The products from an assay or reaction are kept contained in a small volume, which facilitates their detection by fluorescence or other modalities. In addition, monodisperse droplets of nanoliter to picoliter volume can be produced rapidly using microfluidics, and analyzed or sorted on the same microfluidic platform. For these reasons, droplets have been applied to the screening of conditions for protein crystallization, screening of individual biological cells, screening of enzymes for directed evolution, and to construct a detailed, precise dose-response curve for pharmacology.

SUMMARY

Techniques, systems, and devices are disclosed for implementing a droplet array for single-cell analysis.

In one exemplary aspect, a method of conducting single-cell analysis is disclosed. The method comprises generating a plurality of droplets, wherein each of the plurality of droplets contains a core material surrounded by a protective shell; loading the plurality of droplets, via a carrying fluid, onto an array including a plurality of trap structures, wherein the plurality of droplets are held by the plurality of trap structures; selecting a target droplet, held by a trap structure, from the plurality of droplets; and releasing the target droplet from the trap structure.

In another exemplary aspect, an array to facilitate single-cell analysis is disclosed. The array comprises a substrate to allow a carrying fluid to flow; and a plurality of structures positioned on the substrate, wherein each of the structure capable of trapping a droplet comprises: a base for a droplet to be situated on, wherein the base further includes an opening to facilitate release of the droplet from the structure, a first side wall, including a first section and a second section, that extends substantially vertically from the base, and a second side wall, including a first section and a second section, that extends substantially vertically from the base, the first side wall and the second side wall being separated from each other to form a conduit for the carrying fluid to flow therethrough, wherein the first section of the first side wall is substantially parallel to the first section of the second side wall at a first distance to form a first part of the conduit that has a substantially uniform cross-section, and wherein the second section of the first side wall and the second section of the second side wall form a second part of the conduit with a varying cross-section, wherein the second section of the first side wall extends from and is positioned at an angle with respect to the first section of the first wall, and the second section of the second side wall extends from and is positioned at an angle with respect to the first section of the second side wall, such that a cross-section at a junction of the first and second part of the conduit is substantially larger than a cross-section at an end of the second part of the conduit.

In another exemplary aspect, a system of conducting single-cell analysis is disclosed. The system comprises a droplet generator that directs multiple fluid flows toward a junction to generate droplets so that each of the droplets contains a core material surrounded by a protective shell; an array with multiple trap structures to hold the droplets on the array; an incoming conduit connected to the junction to allow the droplets to flow onto the array; one or more outgoing conduits to collect released droplets from the array.

BRIEF DESCRIPTION OF THE DRAWINGS

FIG. 7 shows an exemplary resetting mechanism using reverse flow.

DETAILED DESCRIPTION

Figure 1:
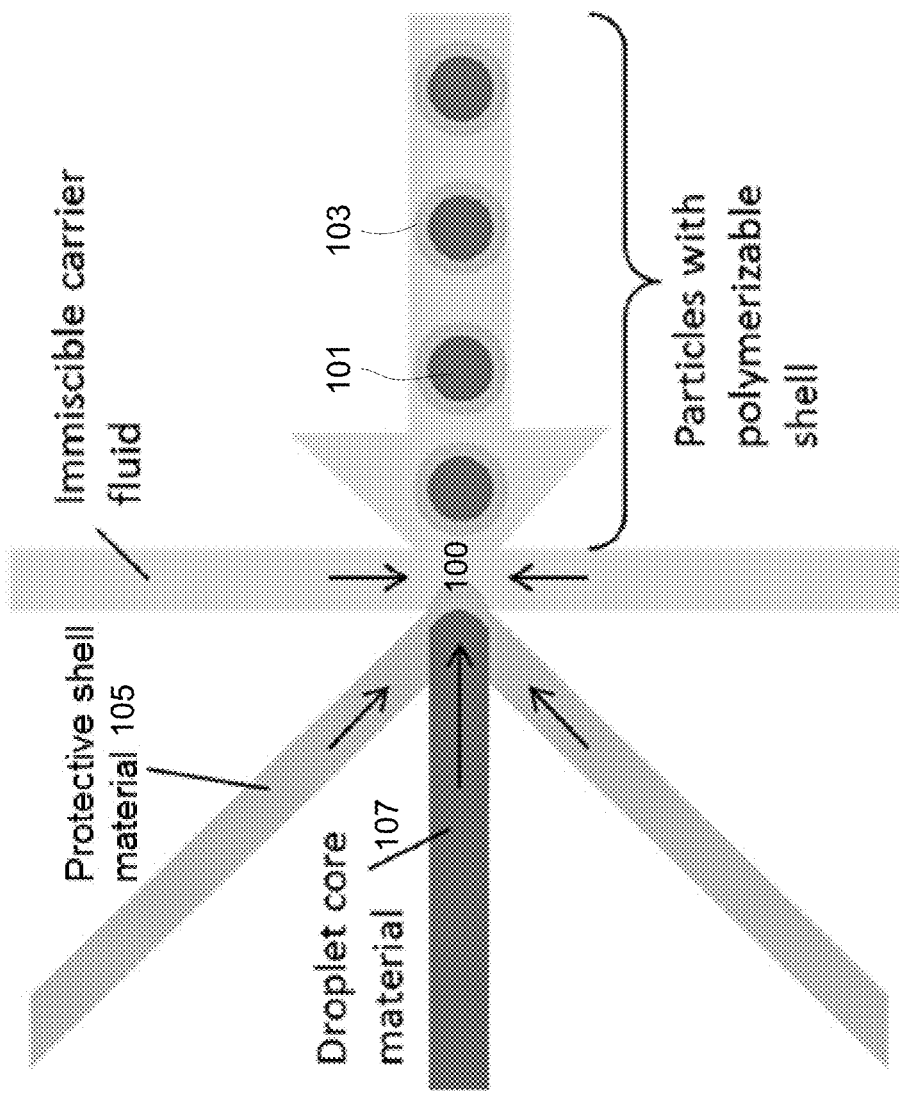
FIG. 1 shows an exemplary schematic configuration to produce droplets with a protective shell.

In this patent document, the word "exemplary" is used to mean serving as an example, instance, or illustration. Any embodiment or configuration described herein as "exemplary" is not necessarily to be construed as preferred or advantageous over other embodiments or configurations. Rather, use of the word exemplary is intended to present concepts in a concrete manner.

Single-cell analysis is an important area for research, especially for cell populations that are heterogeneous. It is helpful to study cell responses at a single cell level because the cell responses can vary a great deal when the entire cell population is present. The traditional methods to study cell behaviors involve examining the aggregated effects of the entire population of cells. However, these methods can mask important trends and signaling within a single cell. To facilitate single-cell analysis, microfluidic droplets are useful to contain single cells in order to isolate the assays and characterization done on each cell. With proper isolation, contamination of cell content between different cells is eliminated.

Fluorescence activated cell sorting (FACS) technology is a popular technique for the purification of cell populations, but requires a relatively large sample (>1 million cells) to perform sorting. Importantly, FACS is unsuitable for detection of rare cells in a population due to the fact that a significant (>90%) portion of the sample is lost or destroyed during processing. Furthermore, FACS sorts cells based on their fluorescent signatures, which limits application of the technique to detection of products produced and maintained inside the cell. Products made and subsequently secreted from individual cells cannot be detected using FACS since these products diffuse into the bulk solution where they are diluted and cannot be traced to the producing cell.

Existing technology to analyze the content of droplets generated on microfluidic platforms consists of array approaches as well as continuous flow approaches. Droplet and single cell arrays enable observation of cells that are isolated or semi-isolated from one another, and can be observed for a period of time. This enables monitoring of processes that can take minutes to hours or more, such as protein production and cell division. However, it is generally not possible to remove a single cell of interest from these arrays. Continuous flow systems to analyze and sort droplets offer a high throughput and the ability to collect droplets containing cells of interest for further study, but do not allow for monitoring of reactions for a long period such as monitoring times exceeding a few minutes or several hours. Increasing the observation time for a reaction often involves adding length to a microfluidic channel in order to preserve the droplet order and thus the droplet's identity. Adding length to a microfluidic channel increases the back pressure of the system and the footprint of the device.

There are several limitations to current technology that preclude the use of microfluidic droplets for certain applications. The current droplet screening technologies produce droplets that are shuttled through a series of microfluidic channels and may or may not undergo analysis on the same platform. In order to identify the contents of the droplets at detection, the order of the droplets is often preserved by maintaining their flow in single-file. This approach limits the throughput of the screening technique. In addition, it limits the time for the reaction or assay to occur, since droplets must usually be kept moving during incubation and increasing microfluidic channel length increases the driving pressure required for the microfluidic chip. In some existing systems, droplets are produced and then incubated off-chip for indefinite periods; however, this requires that droplets to be pooled together which precludes droplet and content identification based on droplet position. Some attempts have been made to include a barcode in each droplet to allow identification of its contents, but this technique greatly increases the complexity of sample preparation.

This patent document describes techniques, systems, and devices that allow for observation of single cells encapsulated in droplets and provide the ability to recover droplets containing a cell of interest. Because the droplets are individually contained in structures and individually addressable, the time duration for which observations can be made are not limited to prior art limitations and thus can be arbitrarily long. The disclosed approach confers a great deal of freedom to the user, since cells of interest may be transported to another microfluidic module or even off-chip for further analysis.

System Overview

Droplets are generated using the disclosed techniques and loaded into an array of traps containing a single droplet each. Once trapped, the droplets may be observed indefinitely and interrogated using optical or electrical observations and measurements. Furthermore, droplets of interest may be removed from the array for further analysis either on- or off the microfluidic device using a number of modalities.

This system provides the unique capability to monitor droplet contents for an extended period of time, combined with the ability to retrieve select droplets on-demand. Some current platforms allow a limited observation/incubation period of a few minutes to a few hours. However, for cell behaviors such as a pathogen invading a host, this limited period is insufficient. There also exist several systems to observe compartmentalized fluid indefinitely on a chip (including microwell systems). However, these systems do not provide a method to remove individual array elements for further study, such as sequencing or mass spectrometry analysis.

The disclosed technologies overcome the limitations of FACS and allow for indefinite, detailed observation of processes, reactions, or assays in droplets over time by capturing and incubating droplets in a static array. In addition, the droplet array technology provides the ability to address and retrieve individual droplets on-demand for further study. Once retrieved, these droplets may be subjected to a wide variety of downstream analyses, including polymerase chain reaction (PCR), sequencing, chromatography and mass spectrometry (e.g. LC-MS or GC-MS), or other analytical techniques.

Examples of Droplet Generation Techniques

Droplets of microliter to picoliter volume can be produced using a microfluidic droplet generator, such as a hydrodynamic flow focuser, so that the droplets contain library of materials to be tested. A droplet generator could be connected to a multiwell plate (such as a 96 well plate) in order to serially deliver different samples for droplet generation and produce droplets with a variety of contents for screening. For example, the droplets can contain library of pathogens to study the process of cell infection by these agents. The droplets can also contain proteins or DNA sequences for conducting processes such as CRISPR inside the droplets. The droplets could also contain antibiotics to study the microbial resistance of bacterial pathogens.

FIG. 1 shows an exemplary schematic configuration for production of droplets with a protective shell. Multiple sheath fluid flows are directed toward a junction 100 to produce droplets. Each droplet may be made up of a core material 101 with a protective shell 103. For droplets that contain desired contents or contents selected for additional analyses or processing, such as containing: a positive assay constituent, a cell or organism of interest, a desired crystallization product, etc., a protective shell of polymerizable material, such as polyethylene glycol-diacrylate (PEG-DA) or gelatin methacryloyl, may be produced so that the content of the droplets can be stored in a more rigid container for subsequent transfer and study. The polymerization may involve formation of a more permanent crosslink, or a reversible crosslink that could allow for breakdown of the polymerizable material using methods such as pH adjustment or UV light exposure. Using a flow focusing junction with multiple channels or nozzles, droplets with a protective shell 105 of the polymer precursor solution would be produced and stored in the array. In some embodiments, the protective shell 105 does not contain polymerizable material. Gel material is used instead to enclose the droplet core material 107. In some embodiments, particles with gel shell are produced first. After the droplets are trapped, the shell may be polymerized in the microfluidic channel by applying e.g. ultraviolet (UV) energy, which will be discussed in further detail in connection with FIG. 5A and FIG. 5B.

Examples of Droplet Interrogation Techniques

Figure 2:
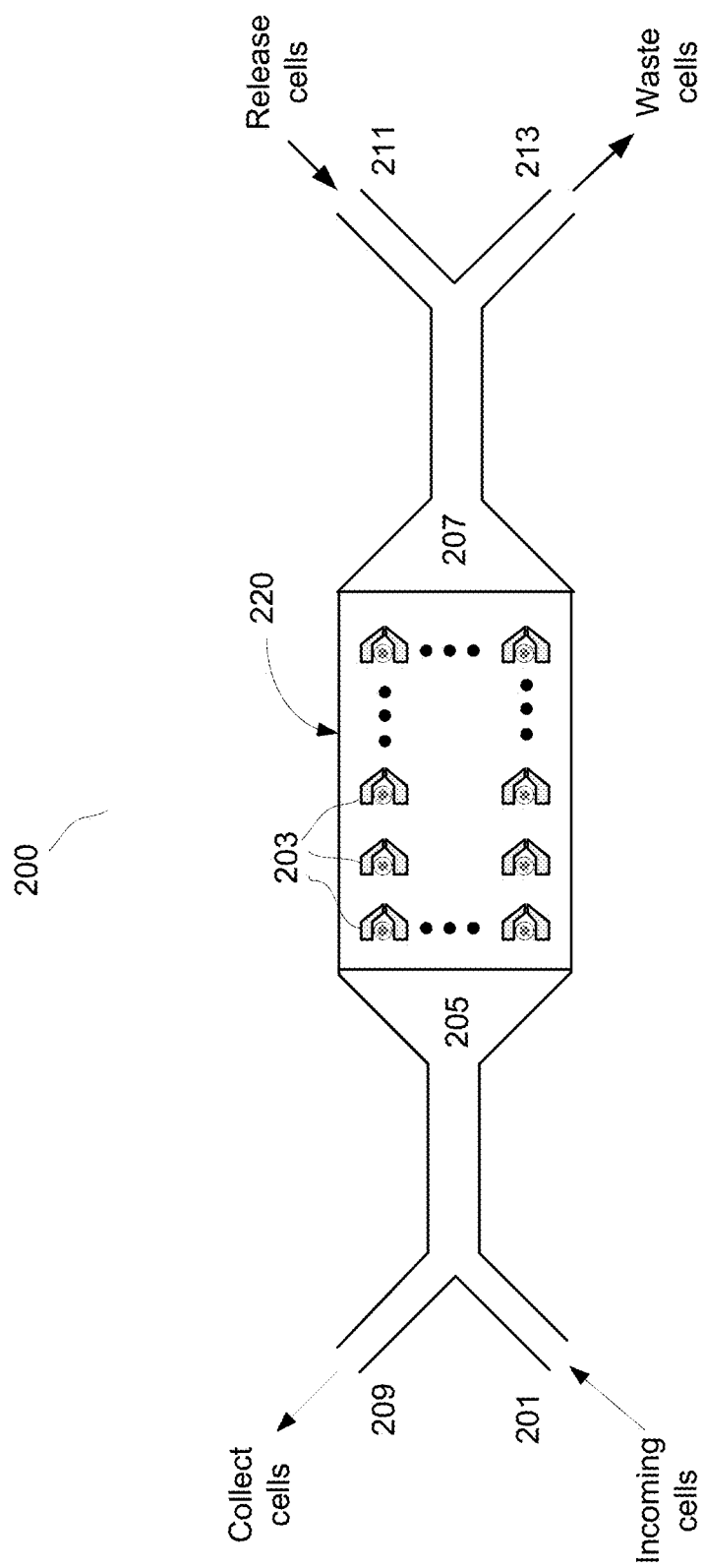
FIG. 2 shows an exemplary schematic diagram of the chamber containing trap structures.

The generated droplets are transported to a large chamber containing structures to trap individual droplets. FIG. 2 shows a schematic diagram of the chamber 200 containing such structures 203.

Figure 3A:
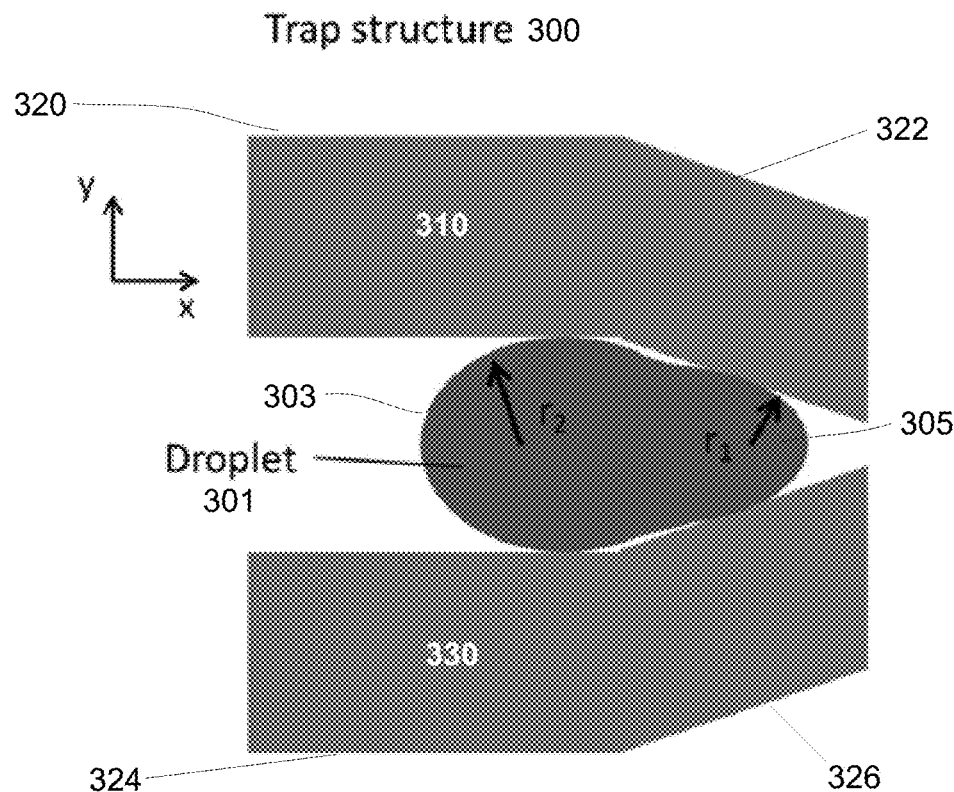
FIG. 3A shows an exemplary trap structure constricting a droplet at its leading edge.
Figure 3B:
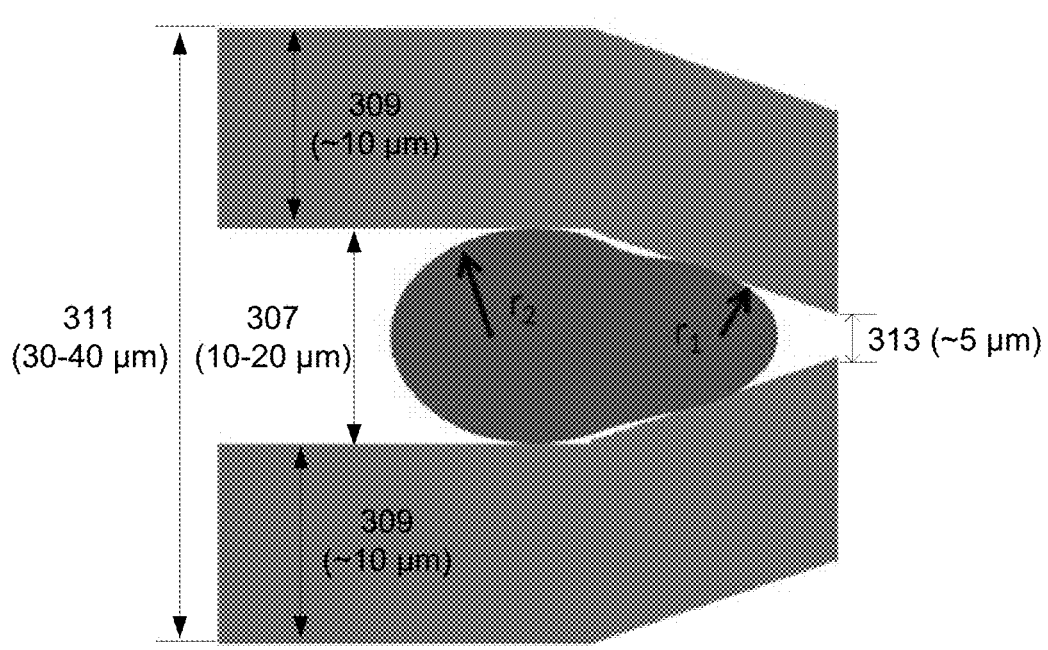
FIG. 3B shows exemplary dimensions for the trap structure.

FIGS. 3A and 3B show greater details of an embodiment of a trap structure 203.

Figure 4:
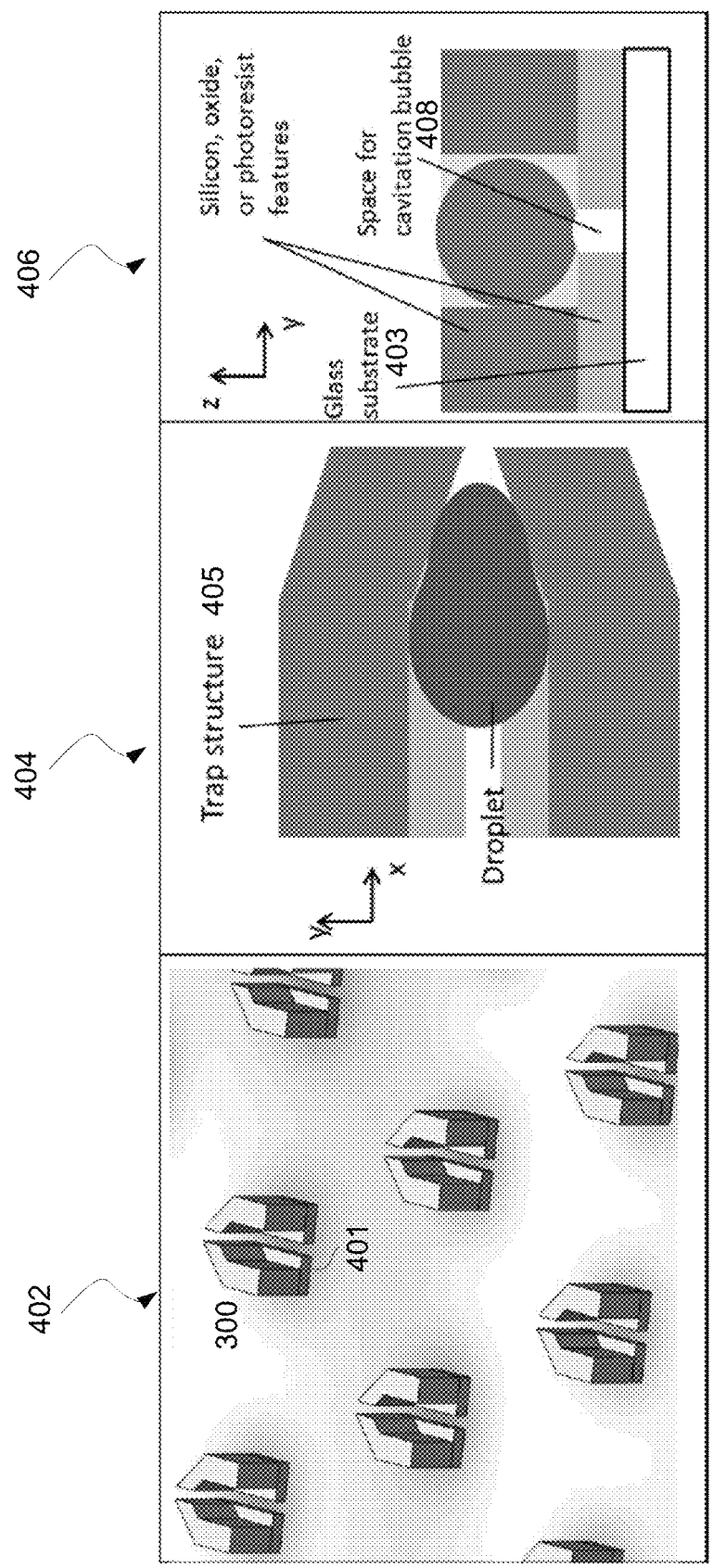
FIG. 4 shows an exemplary design for microfluidic droplet traps with an isometric viewpoint, a top-down view, and a side view of a droplet occupying a trap.

FIG. 4 shows a perspective view and another embodiment of the trap structure 203, as is described further in this document.

FIG. 2 shows an example of a system of conducting single-cell analysis. The system comprises a droplet generator (e.g., as shown in FIG. 1) that directs multiple fluid flows toward a junction to generate droplets so that each of the droplets contains a core material surrounded by a protective shell; an array 220 with multiple trap structures 203 to hold the droplets on the array; an incoming conduit 201 connected to the junction to allow the droplets to flow onto the array; one or more outgoing conduits, e.g. 209, 211, and 213, to collect released droplets from the array.

As depicted in FIG. 2, droplets flow into the trap structures 203 via the incoming conduit 201 and are arrested by a capillary pressure imbalance on the droplet, provided by the trap structure, as further described in greater detail in this document. Capillary pressure at either end of the droplet is dictated by the Young-Laplace equation:

$$\Delta p_{cap} = \gamma \left( \frac{1}{R_x} + \frac{1}{R_z} \right) \quad \text{Eq. (1)}$$

where $R_x$ and $R_z$ are the principle radii of curvature of the droplet in perpendicular directions. FIGS. 3A-3B indicate the radius of curvature at the front and back of the droplet as $r_1$ and $r_2$, respectively. These terms are defined by the following equations, where $r_1$ indicates a dimension at the leading edge of the droplet based on $R_{x,1}$ and $R_{z,1}$ at the leading edge and $r_2$ indicates a dimension at the trailing edge of the droplets based on $R_{x,2}$ and $R_{z,2}$ at the trailing edge:

$$1/r_1 = (1/R_{x,1} + 1/R_{z,1}) \quad \text{Eq. (2)}$$

$$1/r_2 = (1/R_{x,2} + 1R_{z,2}) \quad \text{Eq. (3)}$$

On the incoming side, the chamber 200 may include an opening to which a flowpath 205 may be connected. The flowpath 205 may allow incoming cells to flow in from the incoming conduit 201, and collect cells to be moved out of the chamber 200 via an outlet 209. The outlet 209 and the incoming conduit 201 may be in a fluidic connection with each other prior to being connected to the flowpath 205. The cross-section of the flowpath may taperingly decrease from the diameter of the chamber to the diameter of the fluidic combination of 201 and 209.

In the opposite side of the chamber 200 from the flowpath 205 may be a second opening, leading to a funnel shaped path 207 from which release cells may flow in from a release cell conduit 211 and waste cells may be flown out from a waste cell conduit 213. The conduits 211 and 213 may be in fluidic connection with each other prior to being attached to the funnel shaped path 207.

With reference to FIGS. 3A-3B and FIG. 4, in some embodiments, the trap structure 300 has a base 401 situated on a glass substrate 403 that allows the trap structure 300 to be positioned onto the chamber. The droplet sits on the base 401 once it comes into the trap structure. The base 401 also includes a space 408 that is located beneath the droplet when a droplet is loaded into the trap structure 300. In some embodiments, the space extends at least partially across the base in the x direction (see 404 in FIG. 4). In some embodiments, the space extends at least partially across the base in the y direction. In some embodiment, the space is enclosed within the base 401. The diameter or the width of this space in x or y direction is smaller than the diameter of the droplet so that the droplet does not fall into the space when it is positioned on the base. This space can be filled with the continuous fluid phase (in the case of aqueous droplets, this is an immiscible organic fluid). A thin film of material capable of efficiently absorbing laser energy, such as metal, may be patterned beneath the trap structures. After a droplet is loaded into the trap structure, a laser energy can be applied to the thin film. The thin film absorbs the laser energy as heat, which facilitates formation of a cavitation bubble that expands and pushes the droplet to allow displacement and release of the droplet. Release of the droplet is discussed in further details in connection with FIGS. 8A-8C.

The trap structure 300 also has two side walls 310, 330 that extend substantially vertically from the base. The two side walls 310, 330 are positioned at a distance from each other in the y direction to form a conduit for the carrying fluid to pass through in the x direction, as shown in FIG. 3A. Each of the two side walls may have at least two sections in the x direction. The first section of the first side wall 320 is substantially parallel to the first section of the second side wall 324. The two first sections form a first part of the conduit that has a substantially uniform cross-section. The distance between the first section of the first side wall 320 and the first section of the second side wall 324 is substantially the same as the diameter of the droplet, such that the droplet 301 can easily come into the trap structure via the carrying fluid. The first section of the first side wall 320 and the first section of the second side wall 324 also have a length that is larger than the diameter of the droplet so that a droplet 301 can be completely contained within the trap structure 300 once it is loaded.

Figure 5A:
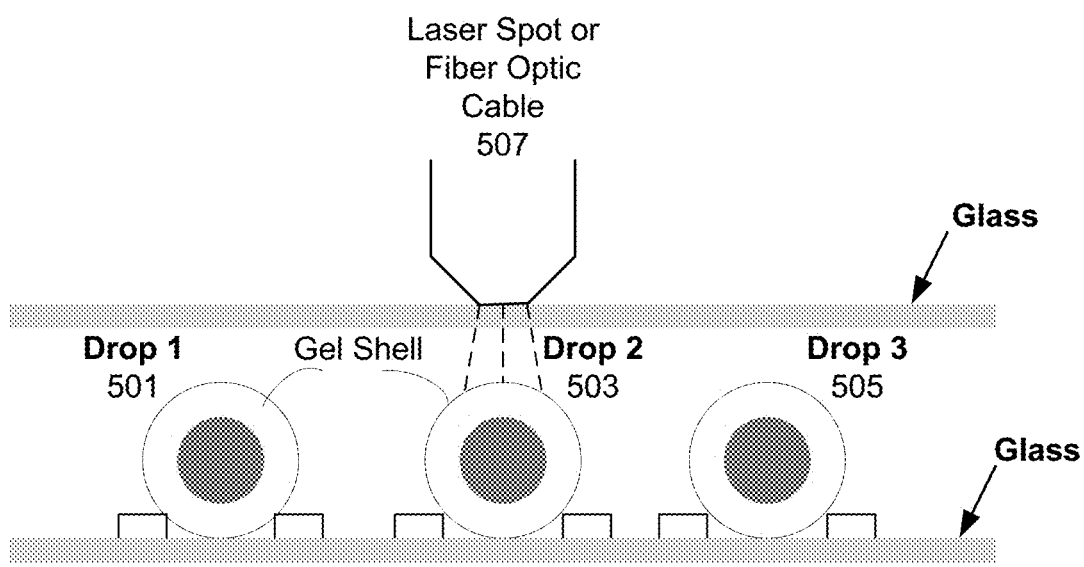
FIG. 5A shows an exemplary process of polymerizing a droplet trapped on the array.
Figure 5B:
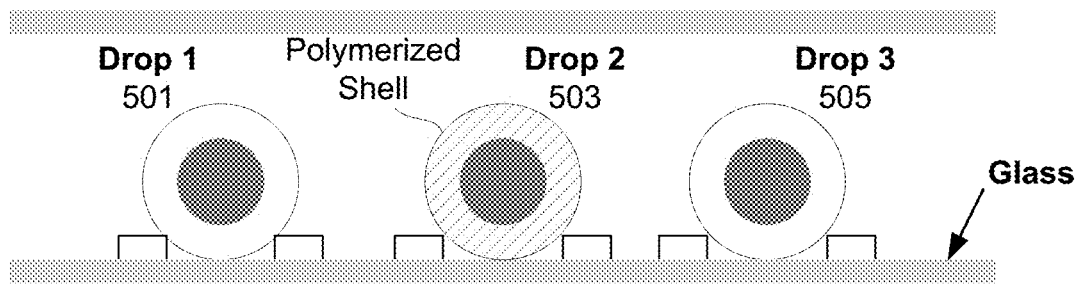
FIG. 5B shows an exemplary diagram of a polymerized droplet and two unpolymerized droplets trapped on the array.

The second section of the first side wall 322 extends from the first section of the first side wall 320. The second section of the first side wall 322 is positioned at an angle with respect to the first section of the first side wall 320 and is directed towards the second side wall 330. Similarly, the second section of the second side wall 326 extends from the first section of the second side wall 324. The second section of the second side wall 326 is positioned at an angle with respect to the first section of the second side wall 324 and is directed towards the first side wall 310. In some embodiments, the second section of the first side wall 322 is symmetrical to the second section of the second side wall 326. The second sections of the first and second side wall 322, 326 form a second part of the conduit. The cross-section of the conduit at the junction of the first and second parts has a substantially larger area than the cross-section at the end of the second part of the conduit. In some embodiment, the second part of the conduit has a tapered shape. The smaller cross-section area of the second part of the conduit is to ensure that the droplet 301 is constricted within the trap structure 300 and cannot pass through the second part of the conduit via the carrying fluid. Accordingly, a droplet moving in the x direction (e.g., from left to right in FIG. 3A), may initially move through a portion of the conduit where the cross-section is uniformly identical, and then may experience a cross-section that tapers, or reduces smoothly and continuously from the cross-section at the inlet of the trap structure to a smaller cross section at the outlet of the trap structure. FIG. 4 and FIGS. 5A and 5B and associated description further disclose some examples of the substrate. Some embodiments of the plurality of structures are also disclosed with respect to FIG. 2, FIGS. 3A-3B and FIG. 4.

In some embodiments, an array to facilitate single-cell analysis may include a substrate and a plurality of structures positioned on the substrate. For example, the substrate may be as described with respect to the glass substrate 403. Other suitable material that allows a carrying fluid to flow may also be used. The plurality of structures positioned on the substrate may be similar to structure and function as described with respect to trap structures 300. For example, as described herein, the structure may be capable of trapping a droplet and include a base for a droplet to be situated on, wherein the base further includes an opening to facilitate release of the droplet from the structure, a first side wall, including a first section and a second section, that extends substantially vertically from the base, and a second side wall, including a first section and a second section, that extends substantially vertically from the base, the first side wall and the second side wall being separated from each other to form a conduit for the carrying fluid to flow therethrough. For example, as depicted and described with respect to FIGS. 3A-3B and FIG. 4, the first section of the first side wall is substantially parallel to the first section of the second side wall at a first distance to form a first part of the conduit that has a substantially uniform cross-section. The second section of the first side wall and the second section of the second side wall may form a second part of the conduit with a varying cross-section. The second section of the first side wall may extend from and may be positioned at an angle with respect to the first section of the first wall, and the second section of the second side wall may extend from and may be positioned at an angle with respect to the first section of the second side wall, such that a cross-section at a junction of the first and second part of the conduit is substantially larger than a cross-section at an end of the second part of the conduit.

When the droplet encounters the trap structure, the substantially round droplet undergoes deformation to have a leading edge and a trailing edge. FIG. 3A shows the trap structure 300 that constricts a droplet 301 at its leading edge 305, so that the radius of curvature at the leading edge of the droplet, $r_1$, is less than the radius of curvature at the trailing edge of the droplet, $r_2$. The trap structures, therefore, force a droplet to adopt a smaller radius of curvature at its leading edge 305, resulting in an higher capillary pressure across this leading edge than the capillary pressure across the trailing edge 303. This pressure imbalance is countered by hydrostatic pressure in the microfluidic channel from the prevailing flow of the immiscible fluid surrounding the droplet, dictated by the Hagen-Pouiseuille equation, which for rectangular microfluidic channels is:

$$\Delta p_{hydrostatic} = \frac{12\mu LQ}{wh^3}\left[1 - \frac{h}{w}\left(\frac{192}{\pi^5}\sum_{n=1,3,5...}^{\infty}\frac{1}{n^5}\tanh\left(\frac{n\pi w}{2h}\right)\right)\right]^{-1} \quad \text{Eq. (4)}$$

where µ is the viscosity of the immiscible phase surrounding the droplets, L is the length of the microfluidic channel, Q is the volumetric flow rate of the fluid, and w and h are the width and height of the microfluidic channel, respectively. The force balance for the system then becomes:

$$F_{total} = (P_{hydrostatic} + P_{cap,x})\int_{A_2}dA - P_{cap,1}\int_{A_1}dA \quad \text{Eq. (5)}$$

where Pcap refers to the capillary pressure at the front or back of the droplet, and can be calculated from Equation (1).

Once a droplet trap is occupied, the fluidic resistance of that path increases and subsequent droplets will flow into unoccupied traps. Thus, droplets may continue to flow into the trapping array until each of the traps is occupied by a single droplet.

The size of the trap structure is determined by the diameters of the target droplets that are to be captured by the trap structure. Typically, a droplets has a diameter of 10-20 µm, which occupies the opening of the first part of the conduit 307. The thickness of the side walls 309 is around 10 µm, leading to a total opening 311 of 30 µm to 40 µm in size. In the particular embodiment shown in FIG. 3B, the size of the opening 313 is around 5 µm. Referring back to FIG. 2, the spacing between traps is at least the diameter of the droplets. The preferred spacing may be at least two times the diameter of the droplet. In some embodiments, a spacing of 100-200 µm is used. The dimensions of the chamber are flexible and depend on the number of droplets needed and also the size of the droplets. In the particular embodiment shown in FIG. 2, a chamber holding 400 droplets has a width of 1965 µm and a length of 3940 µm. In some embodiments, staggering rows of the trap structures on the array improves efficiency of loading the droplets.

The trap structure may be designed to suspend the droplet at a certain height in the microfluidic channel. FIG. 4 shows an exemplary design for microfluidic droplet traps, showing an array of droplet traps from an isometric viewpoint 402, a top-down view 404 of a droplet occupying a trap structure 405, and a side view 406 of a droplet occupying a trap. The side view 406 also shows a designed space for creation of a cavitation bubble underneath a droplet. This feature enables optical observation of the droplet from underneath but also provides a space in which to create a cavitation bubble that can be used to dislodge the droplet from the trap, which will be discussed in further detail in connection with FIGS. 8A-C.

Once trapped, the droplets may be observed using a variety of modalities, including optical (via light or fluorescence microscopy) or electrical (via impedance or admittance measurements). An optical scan can be performed to identify droplets of interest. The droplet shell can also be polymerized on individual droplets via delivery of laser or broadband UV energy under Beer's Law absorption of energy into the droplet shell:

$$\frac{I}{I_0} = e^{-\alpha d} \quad \text{Eq. (6)}$$

where I is the intensity of light that passes through the sample, $I_0$ is the intensity of light transmitted to the sample, α is the absorption coefficient of the material, and d is the thickness of the material.

FIG. 5A shows an exemplary embodiment of polymerizing droplet shell using laser energy. In FIG. 5A there are three droplets positioned on a glass substrate and captured by several trap structures: Drop 1 (501), Drop 2 (503), and Drop 3 (505). All of them have a protective shell made of gel material. By applying laser energy to Drop 2 (503) using a laser spot or a fiber optic cable 507, the protective shell of Drop 2 is polymerized, as shown in FIG. 5B.

Figure 6:
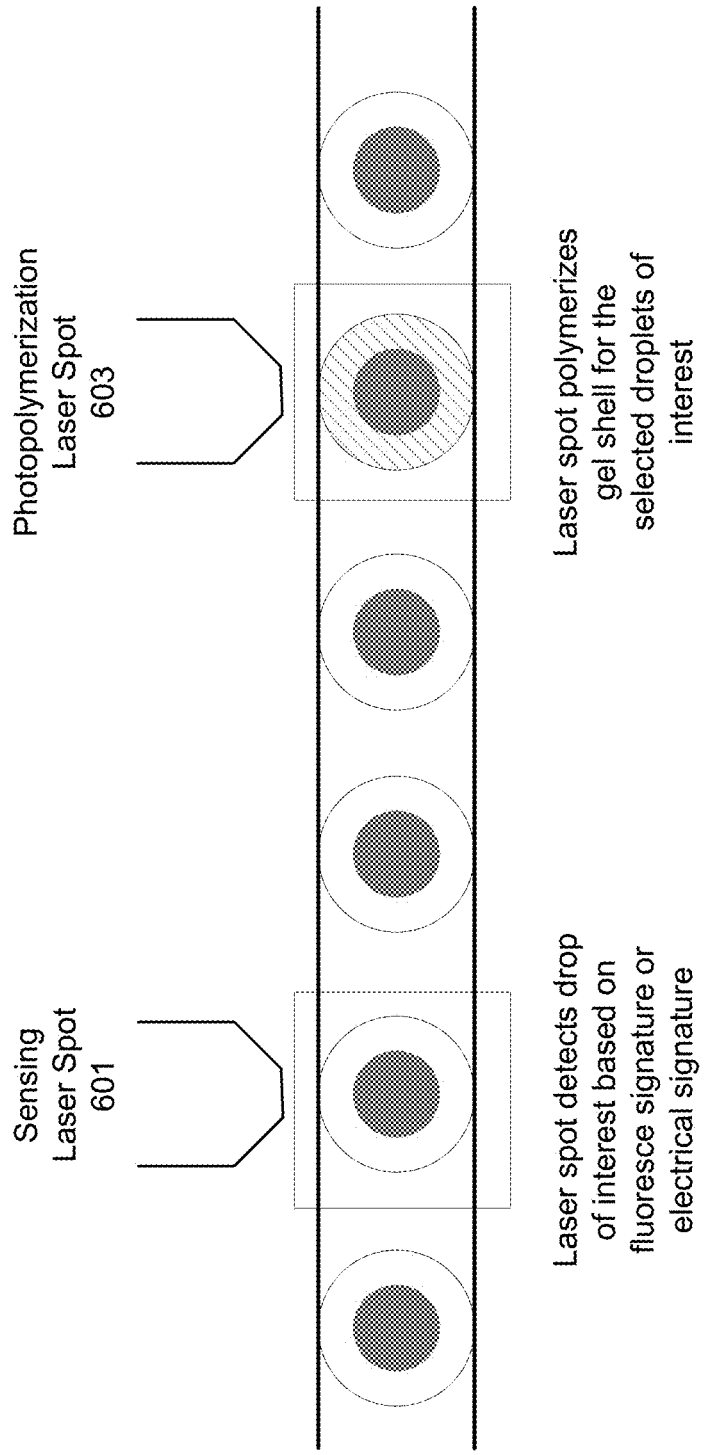
FIG. 6 shows another exemplary interrogation scheme that performs on-the-fly sensing and polymerization of selected droplets using two laser spots.

FIG. 6 shows another exemplary interrogation scheme that performs on-the-fly sensing and polymerization of selected droplets using two laser spots, one for detection and one for actuation. The first laser spot 601 detects drops of interest based on fluorescence intensity. Alternatively, detection of droplets at this spot could be performed using electrical sensing techniques (e.g. electrical impedance or admittance). The second laser spot 603 polymerizes gel shell on the droplets of interest, such as droplets containing a single cell. The droplets may need to enter an incubation chamber prior to interrogation to allow a reaction to occur.

On-Demand Release of Droplets

When the array gets reset, all the droplets captured on the array are released. The array can be reset completely by either inverting the array or reversing flow direction. An exemplary resetting mechanism using reverse flow is demonstrated in FIG. 7.

Figure 10A:
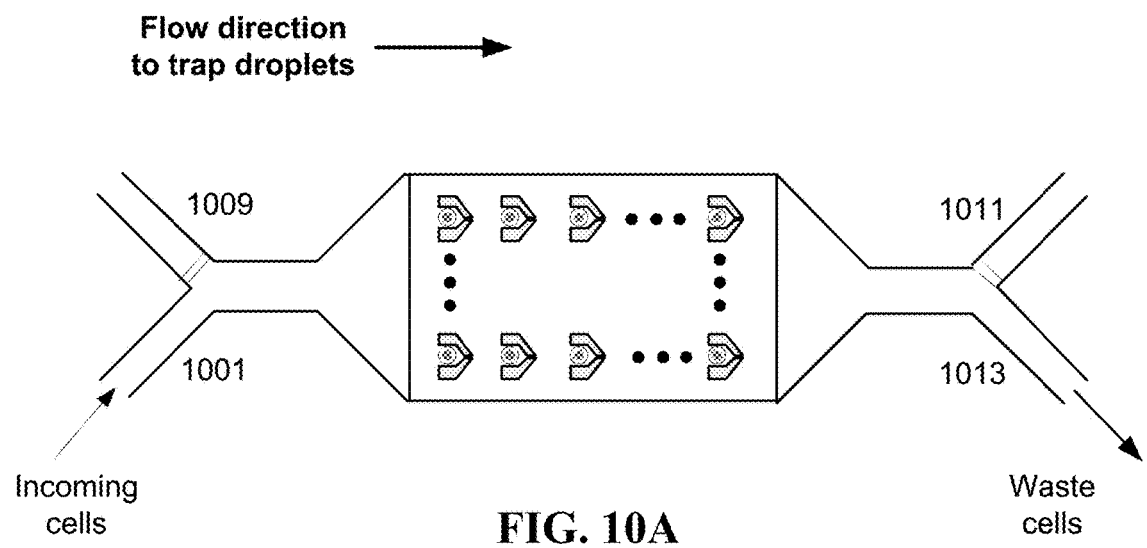
FIG. 10A shows an exemplary embodiment of loading the array with one flow direction.
Figure 10B:
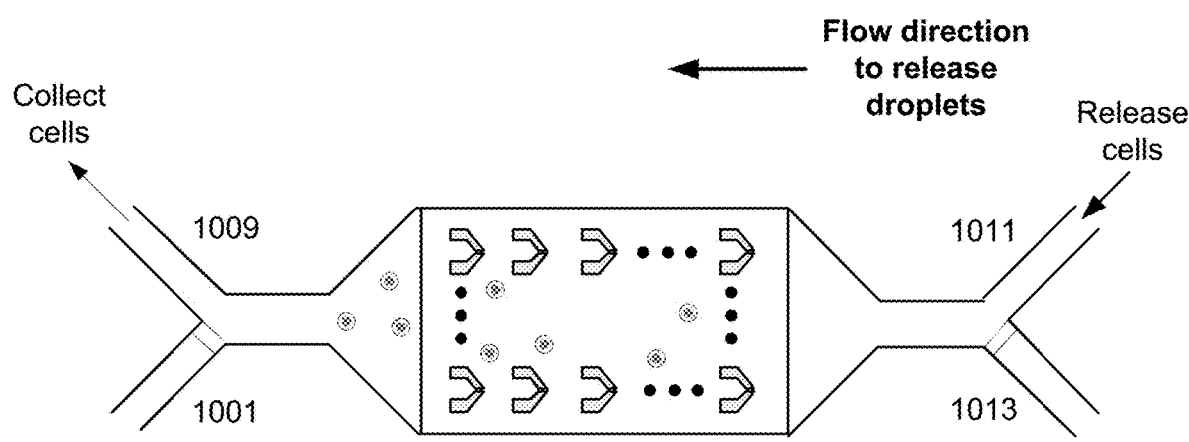
FIG. 10B shows an exemplary embodiment of resetting the array with an opposite flow direction.

FIGS. 10A-10B demonstrate exemplary embodiments of loading and resetting the array using opposite flow directions. In the specific embodiment shown in FIG. 10A, the carrying fluid flows from left to right so that the droplets can be loaded onto the array and captured by the trap structures. The incoming cells come from the incoming conduit 1001. The outlet 1009 and the release cell conduit 1011 are closed during the loading operation. The waste cell conduit 1013 remains open to allow the carrying fluid to flow through. In the embodiment shown in FIG. 10B, the carry fluid changes its direction from right to left to release all the remaining droplets on the array. The release cell conduit 1011 now is open to allow the carrying fluid to flow in the opposite direction. The outlet 1009 is also open to collect all the remaining droplets. The incoming conduit 1001 and the waste conduit 1013 are closed during the reset operation.

Individual droplets of interest may be released from the array using a variety of modalities, including: dielectrophoresis, actuation of fluidic valves, manipulation with lasers or optical tweezers, displacement by acoustic force, displacement by a laser cavitation bubble, magnetic field perturbation (for droplets with inducible contents), or a combination of several of these modalities.

Figures 8A, 8B, 8C:
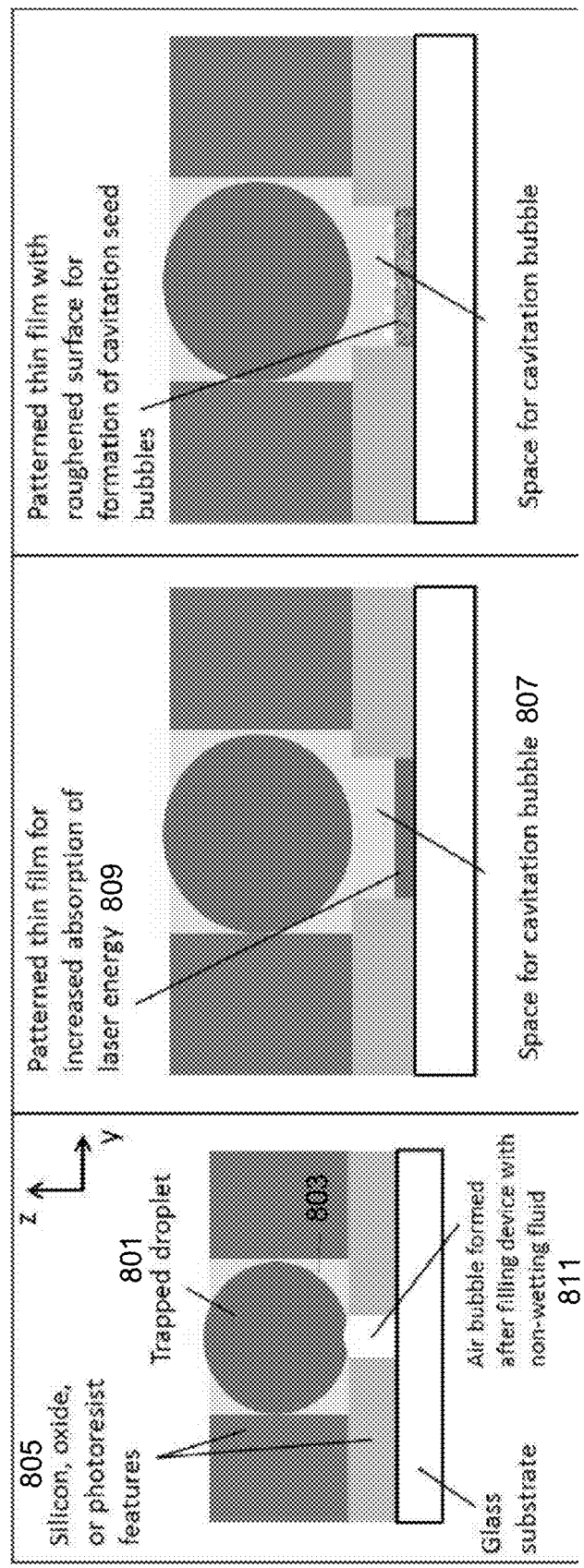
FIGS. 8A-8C show an exemplary configuration to remove droplets from the array using laser cavitation bubbles.

To provide an example of the implementation using laser cavitation bubbles, a Q-switched laser would be implemented to allow delivery of pulsed laser energy to a space located directly below a droplet occupying a trap. FIGS. 8A-8C show an exemplary configuration to remove droplets from the array using laser cavitation bubbles. In FIG. 8A, an aqueous droplet 801 surrounded by an organic shell 803 is trapped in the trap structure 805. A feature of the trap structure is a space 807 underneath the trap to allow a cavitation bubble to form. The laser's wavelength would be selected to match a wavelength of high absorption for the selected film 809, usually an oil such as silicone or mineral oil. Delivery of the pulsed laser energy would produce a cavitation bubble 811 in the space below the droplet 807, which would displace the droplet upward in the z direction and out of the trap. The prevailing flow of the continuous phase would carry the displaced droplet downstream in the chip, where it could be further processed or transported off the chip.

Desired droplets containing a polymerized shell may be removed individually or the entire droplet array may be emptied and droplets with polymerized shells separated from droplets with unpolymerized shells. One technique that may be used to accomplish this type of sorting is viscoelastic droplet sorting. When a droplet is stiffer than the other droplets around it, its movement is affected by the stiffness of the shell. Therefore, a change in shell material affects the trajectory a droplet would take, allowing separation of monodisperse and moderately polydisperse droplet size populations based on viscosity and viscoelasticity differences.

Another method to remove unpolymerized droplets from the array has been described in connection with FIGS. 8A-8C. This approach increases the hydrostatic fluid pressure in the array, such that droplets, whose shells have a lower Young's modulus, would squeeze through the narrow constriction of the droplet trap and flow into waste. Droplets remaining in the array would contain polymerized shells and could be released in a bolus by reversing the flow direction on the array. The viscoelastic drop sorting method and the individual selection method can be used in conjunction with each other.

Exemplary Applications

The disclosed techniques can be used to search for microbes performing a function of interest. For example, *Shewanella oneidensis* can reduce poisonous heavy metal ions by depositing electrons to metal. The disclosed techniques can facilitate the identification of microbes that draw up electrons. The disclosed techniques can also be used to culture individual or small number of microbes in droplets, then stimulate them electrically and analyze the responses. Currently, metatranscriptomic mRNA analysis is used to identify changes in microbial communities. Due to the limitation of the current technology, it is difficult to isolate variables within the microbe community. Also, the entire microbe community can shift genetic expression. The use of disclosed techniques facilitates the isolation of variables and allows accurate observation of the changes in microbial communities.

Figure 9:
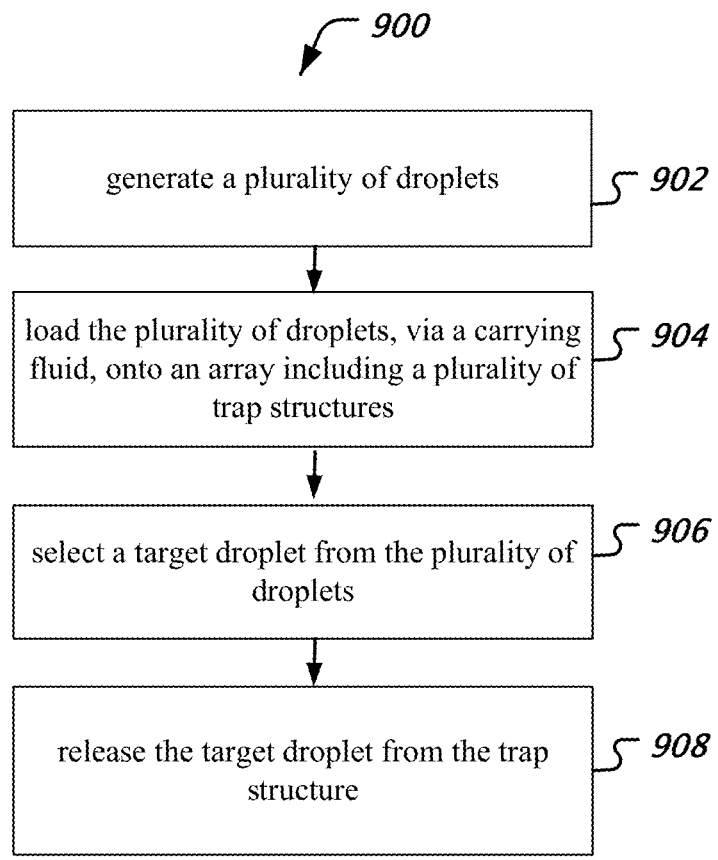
FIG. 9 shows an exemplary flowchart for a method of conducting single-cell analysis.

FIG. 9 shows an exemplary flowchart for a method 900 of conducting single-cell analysis. The method includes, at 902, generating a plurality of droplets, wherein each of the plurality of droplets contains a core material surrounded by a protective shell. The method includes, at 904, loading the plurality of droplets, via a carrying fluid, onto an array including a plurality of trap structures, wherein the plurality of droplets are held by the plurality of trap structures. The method includes, at 906, selecting a target droplet, held by a trap structure, from the plurality of droplets. The method further includes, at 908, releasing the target droplet from the trap structure.

In some embodiments, the method includes observing the target droplet for an indefinite amount of time. In some embodiments, the method includes modifying the core material of the target droplet. The method may also include collecting the target droplet to transfer to a different platform and/or resetting the array by releasing remaining of the plurality of droplets on the array.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A method of conducting single-cell analysis, comprising:
    generating a plurality of droplets, wherein each of the plurality of droplets contains a core material surrounded by a protective shell;
    loading the plurality of droplets, via a carrying fluid, onto an array, wherein the array includes a plurality of trap structures that are capable of holding the plurality of droplets, wherein each of the plurality of trap structures comprises:
        a base for a droplet to be situated on, wherein the base further includes an opening to facilitate release of the droplet from the trap structure,
        a first side wall, including a first section and a second section,
        a second side wall, including a first section and a second section,
        the first side wall and the second side wall being separated from each other to form a conduit for the carrying fluid to flow therethrough,
        wherein the first section of the first side wall is substantially parallel to the first section of the second side wall at a first distance to form a first part of the conduit that has a substantially uniform cross-section, and
        wherein the second section of the first side wall and the second section of the second side wall form a second part of the conduit with a varying cross-section, wherein the second section of the first side wall extends from and is positioned at an angle with respect to the first section of the first wall, and the second section of the second side wall extends from and is positioned at an angle with respect to the first section of the second side wall, such that a cross-section at an end of the second part of the conduit is smaller than a cross-section of the substantially uniform cross-section of the first part of the conduit;
    selecting a target droplet from the plurality of droplets, the target droplet being held by a trap structure of the plurality of trap structures; and
    releasing the target droplet from the trap structure.

2. The method of claim 1, further comprising:
    preserving observability of the target droplet for a time period exceeding a pre-defined time interval, wherein the pre-defined time interval is at least 2 hours.

3. The method of claim 1, further comprising:
    modifying, after selecting the target droplet from the plurality of droplets, the core material of the target droplet.

4. The method of claim 1, further comprising:
    collecting the target droplet to transfer to a different platform.

5. The method of claim 1, further comprising:
    resetting the array by releasing remaining of the plurality of droplets on the array.

6. The method of claim 5, wherein the resetting comprises:
    inverting the array, or
    reversing flow direction of the carrying fluid.

7. The method of claim 1, wherein the generating comprises directing multiple fluid flows toward a junction, wherein the multiple fluid flows include:
    a first fluid flow that contains the core material, and
    a second fluid flow that contains the carrying fluid.

8. The method of claim 7, wherein the multiple fluid flows further include a third fluid flow that contains a material for the protective shell.

9. The method of claim 8, wherein the material for the protective shell includes a polymerizable material.

10. The method of claim 1, wherein the selecting comprises performing an optical scan or an electrical scan of the plurality of droplets.

11. The method of claim 9, wherein the selecting comprises polymerizing the protective shell of the target droplet.

12. The method of claim 1, wherein the releasing is performed by dielectrophoresis, actuation of fluidic valves, displacement by acoustic force, magnetic field perturbation, or a combination thereof.

13. The method of claim 1, wherein the releasing comprises displacing the target droplet by delivering a laser energy to the trap structure to form a cavitation bubble under the target droplet.

14. An array to facilitate single-cell analysis, comprising:
    a substrate to allow a carrying fluid to flow; and
    a plurality of structures disposed on the substrate, wherein each of the plurality of structures comprises:
        a base for a droplet to be situated on, wherein the base further includes an opening to facilitate release of the droplet from the structure,
        a first side wall, including a first section and a second section, that extends substantially vertically from the base, and
        a second side wall, including a first section and a second section, that extends substantially vertically from the base,
        the first side wall and the second side wall being separated from each other to form a conduit for the carrying fluid to flow therethrough,
        wherein the first section of the first side wall is substantially parallel to the first section of the second side wall at a first distance to form a first part of the conduit that has a substantially uniform cross-section, and
        wherein the second section of the first side wall and the second section of the second side wall form a second part of the conduit with a varying cross-section, wherein the second section of the first side wall extends from and is positioned at an angle with respect to the first section of the first wall, and the second section of the second side wall extends from and is positioned at an angle with respect to the first section of the second side wall, such that a cross-section at a junction of the first and second part of the conduit is substantially larger than a cross-section at an end of the second part of the conduit.

15. The array of claim 14, wherein the plurality of structures are staggered.

16. The array of claim 14, wherein the plurality of structures are separated from each other by a distance larger than a diameter of the droplet.

17. The array of claim 14, wherein the opening extends at least partially across the base.

18. The array of claim 14, where in the opening includes a thin film that allows a cavitation bubble to form to facilitate the release of the droplet.

19. The array of claim 14, wherein distance between the first section of the first side wall and the first section of the second side wall is substantially the same as a diameter of the droplet.

20. The array of claim 19, where in the first section of the first side wall has a length that is larger than the diameter of the droplet.

21. The array of claim 19, where in the first section of the second side wall has a length that is larger than the diameter of the droplet.

22. The array of claim 14, wherein the second section of the first side wall is symmetrical to the second section of the second side wall.

23. The array of claim 14, wherein the second part of the conduit has a tapered shape.

24. The array of claim 14, wherein the first side wall and the second side wall have a thickness of around 10 µm.

25. A system of conducting single-cell analysis, comprising:
   a droplet generator that directs multiple fluid flows toward a junction to generate droplets so that each of the droplets contains a core material surrounded by a protective shell;
   an array with multiple trap structures to hold the droplets on the array, wherein each trap structure of the multiple trap structures comprises:
      a base for a droplet to be situated on, wherein the base further includes an opening to facilitate release of the droplet,
      a first side wall, including a first section and a second section, and
      a second side wall, including a first section and a second section,
      the first side wall and the second side wall being separated from each other to form a conduit for the carrying fluid to flow therethrough,
      wherein the first section of the first side wall is substantially parallel to the first section of the second side wall at a first distance to form a first part of the conduit that has a substantially uniform cross-section, and
      wherein the second section of the first side wall and the second section of the second side wall form a second part of the conduit with a varying cross-section, wherein the second section of the first side wall extends from and is positioned at an angle with respect to the first section of the first wall, and the second section of the second side wall extends from and is positioned at an angle with respect to the first section of the second side wall, such that a cross-section at an end of the second part of the conduit is smaller than a cross-section of the substantially uniform cross-section of the first part of the conduit;
   an incoming conduit connected to the junction to allow the droplets to flow onto the array; and
   one or more outgoing conduits to collect released droplets from the array.

26. The system of claim 25, further comprising:
a first laser source to scan the droplets to identify a target droplet.

27. The system of claim 26, further comprising:
a second laser source to polymerize the protective shell of the target droplet.

28. The system of claim 25, further comprising:
a thin film located within a space extending at least partially across the base in one direction, and
a third laser spot to deliver laser energy to the thin film to form a bubble to facilitate release of the droplet.

* * * * *